United States Patent
Bhadra et al.

(10) Patent No.: US 7,142,925 B1
(45) Date of Patent: Nov. 28, 2006

(54) COMBINED STIMULATION OF VENTRAL AND DORSAL SACRAL ROOTS FOR CONTROL OF BLADDER FUNCTION

(75) Inventors: Narendra Bhadra, Cleveland Heights, OH (US); J. Thomas Mortimer, Chagrin Falls, OH (US); Volker Grunewald, Hannover (DE)

(73) Assignee: Axon Engineering, Inc., Cleveland, OH (US)

( * ) Notice: Subject to any disclaimer, the term of this patent is extended or adjusted under 35 U.S.C. 154(b) by 0 days.

(21) Appl. No.: 09/787,244

(22) PCT Filed: Sep. 14, 1999

(86) PCT No.: PCT/US99/21049

§ 371 (c)(1),
(2), (4) Date: May 16, 2001

(87) PCT Pub. No.: WO00/15293

PCT Pub. Date: Mar. 23, 2000

Related U.S. Application Data

(60) Provisional application No. 60/100,542, filed on Sep. 16, 1998.

(51) Int. Cl.
*A61N 1/36* (2006.01)
(52) U.S. Cl. ...................... 607/41
(58) Field of Classification Search .......... 607/40, 607/41, 117, 118, 133, 138, 116
See application file for complete search history.

(56) References Cited

U.S. PATENT DOCUMENTS

| | | | | |
|---|---|---|---|---|
| 3,650,276 A | * | 3/1972 | Burghele et al. | 607/40 |
| 3,870,051 A | * | 3/1975 | Brindley | 607/40 |
| 4,406,288 A | * | 9/1983 | Horwinski et al. | 607/41 |
| 5,199,430 A | * | 4/1993 | Fang et al. | 607/40 |

FOREIGN PATENT DOCUMENTS

| EP | 0245547 | * 11/1987 |
|---|---|---|
| EP | 0245547 A1 | * 11/1987 |

* cited by examiner

*Primary Examiner*—George R. Evanisko
(74) *Attorney, Agent, or Firm*—Jerrold J. Litzinger

(57) ABSTRACT

Methods and apparatuses for controlling bladder discharge in a patient are described. The method includes coupling a first electrode to a sacral ventral root of the patient and coupling a second electrode to a sacral dorsal root of the patient. The method may be applied to spinal cord injured patients without dorsal root section.

16 Claims, 2 Drawing Sheets

Average Voided Volumes During a 10 Second Pulse Train
I/Q = Intermittent surface stimulation with Quasitrapezoidal motor pulses
C/Q = Continuous surface stimulation with Quasitrapezoidal motor pulses
I/R = Intermittent surface stimulation with Rectangular motor pulses
C/R = Continuous surface stimulation with rectangular motor pulses

COMBINED STIMULATION OF VENTRAL AND DORSAL SACRAL ROOTS FOR CONTROL OF BLADDER FUNCTION

CROSS REFERENCE TO RELATED APPLICATIONS

This is a utility patent application taking priority from provisional patent application 60/100,542, filed Sep. 16, 1998, which is incorporated herein by reference.

BACKGROUND OF THE INVENTION

1. Field of Invention

This invention relates generally to selective nerve stimulation for bladder control, and, in particular, to a technique by which micturition can be achieved in spinal cord injured patients without dorsal root section.

2. Description of the Prior Art

Retention of urine, leading to complications such as urinary tract infection and urinary calculi, remains a major factor leading to morbidity in spinal cord injured patients. In high cord injury, with upper motor neuron damage, the lower nerve pathways to the bladder are intact. The aim of micturition control in these individuals is to enable them to contract the bladder musculature without activating structures in the urethra that may impede urine flow. The procedure should leave an acceptable post-void residual volume within the bladder and should also be able to prevent overflow incontinence.

The difference in the size of the nerve fibers to the bladder or bowel and the urethral or anal sphincter allows the development of techniques to selectively activate the nerves to the bladder and bowel without the activation of the sphincters.

Previously, electrical stimulation has been applied to control the bladder and bowel. The previous attempts have focused on three techniques: direct stimulation of the detrusor muscle, activation of the detrusor by stimulation of the conus medullaris, and activation of the detrusor by sacral root or nerve stimulation with extensive dorsal rhizotomy. All three of these methods suffer from the same problem. They all cause contraction of the bladder to expel urine concurrently with contraction of the external urethral sphincter blocking urine flow. The rhizotomy technique also results in the loss of erection for the male. It would be advantageous if contraction of the sphincter could be selectively blocked.

Techniques available for blocking nerve impulses are discussed, for example, in "A Technique for Collision Block of Peripheral Nerve: Single Stimulation Analysis", van den Honert and Mortimer, IEEE Transactions on Biomedical Engineering, Volume BME-28, No. 5, May 1981, pages 373–378, and "Generation of Unidirectionally Propagated Action Potentials in a Peripheral Nerve by Brief Stimuli", van den Honert and Mortimer, Science, Volume 206, December 1979, pages 1311–1312. With the van den Honert and Mortimer techniques, a nerve impulse or action potential is generated which travels toward the brain. When the artificially generated nerve impulse meets a motor impulse travelling from the brain, the motor impulse is collision blocked. That is, the artificially generated action potential cancels the motor action potential. If one were to apply the van den Honert and Mortimer techniques, it could be used to cause concurrent relaxation of both the bladder contracting muscles and the urethral sphincter.

Sacral nerve stimulation for electrical control of bladder function has been attempted for many years; however, virtually all attempts have been plagued by problems associated with co-activation of contractile structures in the urethra that impede urine flow. One such attempt is described in U.S. Pat. No. 4,607,639, which issued to Tanagho, et al. This patent describes a technique in which the sacral nerves are separated to isolate the ventral and dorsal roots thereof, and the inferior somatic nerve S1 is sectioned to isolate the external sphincter on one side. The dorsal root of S2 is then sectioned unilaterally to isolate the sensory function thereof. An electrode is positioned on the S3 sacral nerve to stimulate the detrusor muscles of the bladder. However, it is suggested that sphincter response may be reflexly produced using this technique, and mentions the necessity for the rhizotomy of the dorsal roots.

U.S. Pat. No. 5,199,430 teaches a system for selectively arresting propagation of action potentials in large diameter fibers without arresting propagation in small diameter nerve fibers using a quasitrapezoidal waveform. This waveform, which is disclosed in U.S. Pat. No. 4,608,985, and its stimulation scheme made it possible to install electrodes on the sacral roots that could differentially activate the small fibers to the detrusor and rectum without activating the large fibers to the sphincter, thus allowing bladder and bowel activation without the sphincter tone being raised. However, this procedure often involved dorsal rhizotomy to minimize any reflexogenic response.

The present invention contemplates a new technique for bladder function control in which a dorsal rhizotomy is unnecessary.

SUMMARY OF THE INVENTION

Accordingly, it is an object of the present invention to provide a system and method for inducing micturition in spinal cord injured patients.

It is a further object of the present invention to provide a method of controlling bladder draining by stimulating nerve cuff electrodes implanted on the sacral motor roots and also the sacral sensory roots.

It is a still further object of the present invention to provide a method of efficiently voiding the bladder of a patient without performing a dorsal rhizotomy.

These and other objects are accomplished in the present invention by a method and system for selectively controlling activation of a patient's bladder by applying trains of quasitrapezoidal pulses with appropriate current amplitudes on both the ventral and dorsal sacral roots to subdue urethral reflexes and enhance voiding.

DETAILED DESCRIPTION OF THE PREFERRED EMBODIMENTS

Figure 1:
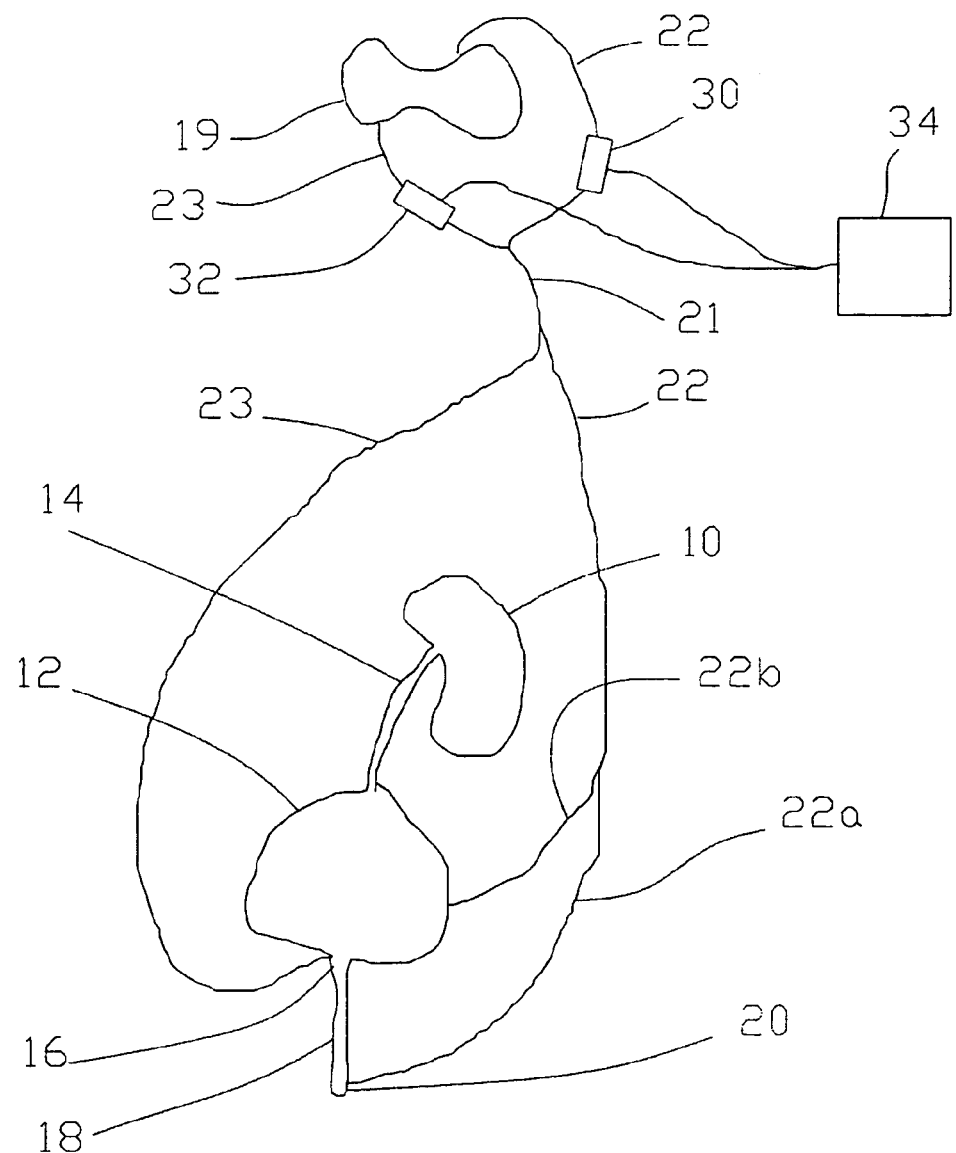
FIG. 1 schematically illustrates the placement of electrodes for controlling the bladder in the present invention.

Referring now to FIG. 1, there is shown an illustrative embodiment of the present invention within the environment of the human body. Kidney 10 is connected to the bladder 12 via the ureter 14, which carries away urine from kidney 10 to bladder 12. Urine is expelled from the body through bladder neck 16 and urethra 18 and out from urethral sphincter 20. Bladder 12 and sphincter 20 function is controlled by action potentials traveling from spinal cord 19 primarily, but not limited to, on a pair of sacral roots 21 which consists of a segment of ventral sacral roots 22 and a segment of dorsal sacral roots 23. Dorsal roots 23 are primarily sensory (afferent) to transmit sensation to spinal cord 19, while ventral roots 22 primarily transmit motor pulses (efferent) from spinal cord 19 to bladder 12 and sphincter 20. Although illustrated as being separated, the dorsal and ventral roots for each nerve are, in fact, normally joined together and their fibers mixed to progress as a single trunk.

Ventral roots 22 include nerve bundles 22a which include larger diameter nerve fibers and nerve bundles 22b which include smaller diameter fibers. Larger fibers 22a connect between spinal cord 19 and sphincter 20, while smaller fibers 22b connect between spinal cord 19 and bladder 12. Action potentials flowing along larger fibers 22a cause sphincter 20 to contract, blocking the outlet from urethra 18. When the bladder is to be emptied, the flow of action potentials through fibers 22a is stopped, allowing sphincter 20 to relax.

Smaller fibers 22b usually carry no action potentials until the person desires to evacuate the bladder; action potentials are then sent along fibers 22b concurrently with the stopping of action potentials along fibers 22a, causing sphincter 20 to relax and allowing bladder neck 16 to open concurrently with bladder 12 muscles contracting, thus expelling urine.

Spinal cord injuries and various other medical conditions can cause a loss of control of the bladder function. To reinstitute this control, a cuff electrode 30 can be mounted surrounding sacral ventral root 22. Cuff electrode 30, which is preferably a self-curling spiral electrode that is biased to curl around the selected root and is described in U.S. Pat. No. 4,602,624, is configured to accommodate nerves of varying diameters and can electrically excite action potentials on smaller fibers 22b while blocking naturally occurring and electrically activated action potentials from travelling downstream on larger fibers 22a. An example of this procedure is described in detail in U.S. Pat. No. 5,199,430, which issued in Apr. 6, 1993, and is hereby incorporated by reference in its entirety.

The present invention also includes an additional cuff electrode 32 which is implanted on a dorsal sacral root 23. Application of trains of quasitrapezoidal pulses, which are described and taught in U.S. Pat. No. 4,608,985, which patent is incorporated herein by reference, that have appropriate current amplitudes and are applied concurrently to electrodes 30 and 32 to stimulate the dorsal and ventral roots can result in the voiding of bladder contents without increasing sphincter pressures. A controller 34 is electrically coupled to electrodes 30 and 32 to provide the necessary signals for this desired bladder control.

Several experiments were conducted to confirm that combined dorsal and ventral root stimulation provides an effective low pressure bladder evacuation without requiring dorsal rhizotomy.

EXPERIMENT 1

Combined sensory and motor stimulus was applied to an animal under 2.5% halothane inhalation anesthesia. An efferent motor stimulus was applied by a spiral nerve cuff electrode implanted on S2 motor roots. Either a quasitrapezoidal, balanced biphasic, 20 Hz pulse, with current amplitude set at a volume determined to selectively block sphincter activity, or a conventional rectangular supra-threshold stimulus was used. The efferent sensory stimulus was applied to the S2 dermatome with surface electrodes using a 20 Hz balanced biphasic rectangular pulse at 10 to 15 ma. The surface stimulus was varied to be continuous or intermittent (1 second on/1 second off). The bladder was filled before each trial run with 60 ml of sterile saline.

Figure 2:
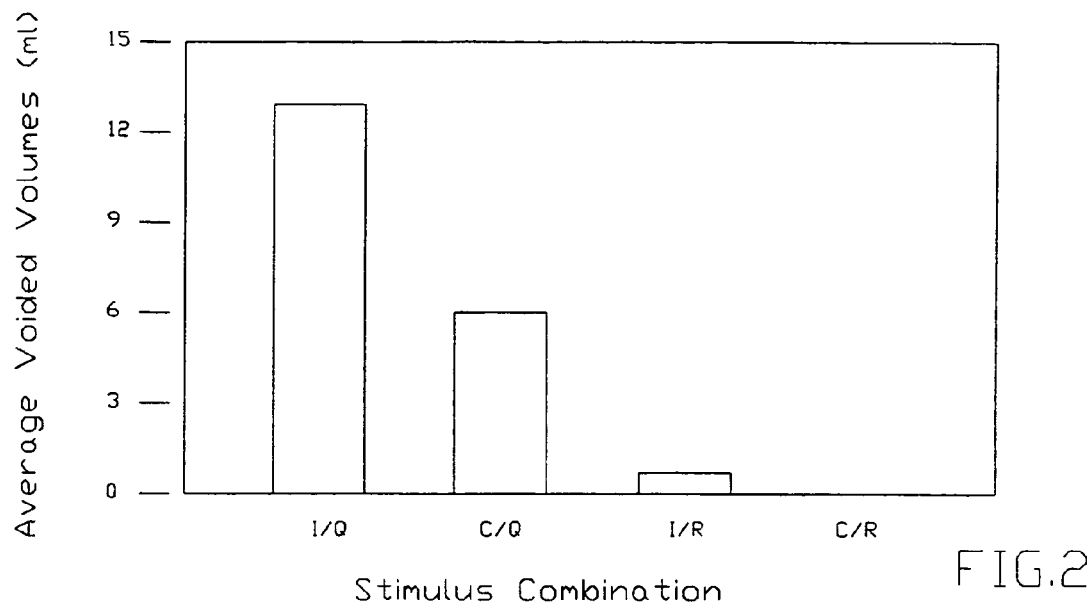
FIG. 2 is a graphic representation showing average voided volume from different combinations of stimulus.

FIG. 2 shows the average volume of fluid voided during a 10 second pulse train for each combination of stimulus trains. The results show that a combination of selective motor root activation by a quasitrapezoidal pulse train and intermittent surface stimulation to the S2 determatome enhanced bladder emptying.

EXPERIMENT 2

Combined sensory and motor stimulus was applied to an animal under 2.5% halothane inhalation anesthesia. The motor stimulus was applied by a spiral nerve cuff electrode implanted on the S2 motor roots. A quasitrapezoidal, balanced biphasic, 20 Hz pulse, with current amplitude set at a value determined to selectively block sphincter activity, was used. The sensory stimulus was applied to S1, S2, or S3 dermatome with surface electrodes using a 20 Hz balanced biphasic rectangular pulse at 10 to 15 ma. The intermittent surface stimulation was varied to be either 1 second on/1 second off or 0.5 seconds on/0.5 seconds off. The tests were randomized for stimulus combinations. The test results show that bladder emptying was enhanced only when the combined sensory stimulus was applied to the S2 dermatome. The 1 second on/1 second off intermittent pattern was more effective than the 0.5 seconds on/0.5 seconds off pattern.

EXPERIMENT 3

Combined stimulation of the dorsal and ventral sacral roots was applied to an animal by implanting spiral nerve cuff electrodes on the sacral ventral motor roots at S2 and S3, while leaving the dorsal roots intact and implanting a spiral nerve cuff electrode on one dorsal S2 root. The ventral sacral roots were stimulated with quasitrapezoidal pulse trains at 20 Hz with current amplitudes sufficient to selectively activate the bladder or with 20 Hz conventional rectangular pulses. At the same time, a 20 Hz intermittent stimulus, 1 second on/1 second off was applied to the S2 dorsal root.

Figure 3:
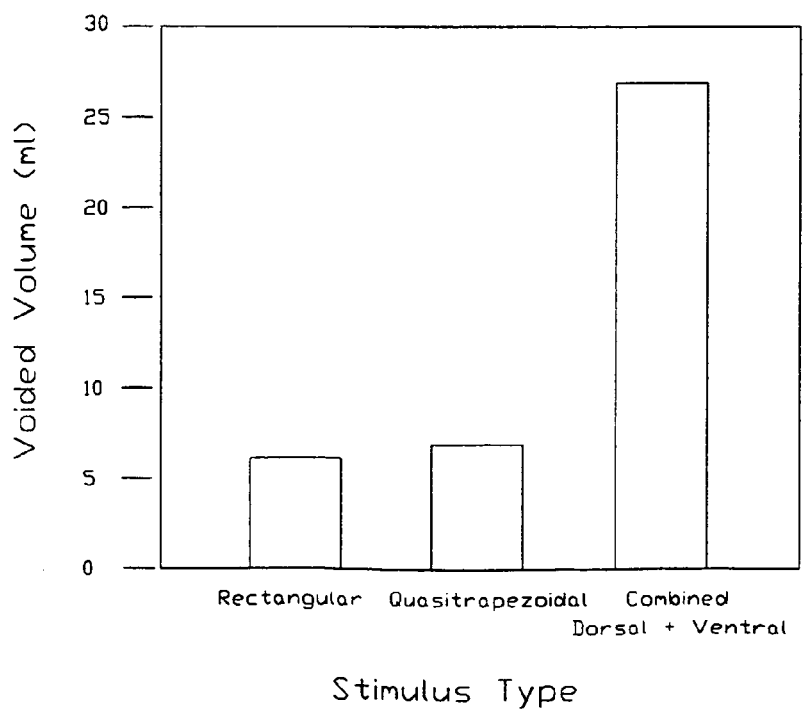
FIG. 3 is a graphic representation showing average voided volume when combined dorsal and ventral root stimulation is used.

Table 1 shows the average results from three trials for each stimulus pattern. For 10 seconds of motor stimulation, an average increase of 66% in flow rate was observed during combined motor and sensory stimulation, while FIG. 3 shows the average volumes voided.

TABLE 1

| Pulse Type | Qmax | V (ml) | Pv (Qmax) | Pu (Qmax) | Pv max | Pu max |
|---|---|---|---|---|---|---|
| 20 Hz R | 2.3 | 6.0 | 50.0 | 40.0 | 117.5 | 160.0 |
| 20 Hz Q | 2.4 | 7.0 | 78.8 | 57.5 | 111.3 | 99.4 |
| Aff + 20 Hz Q | 4.0 | 27.0 | 59.2 | 51.7 | 85.0 | 80.0 |

Figure 4:
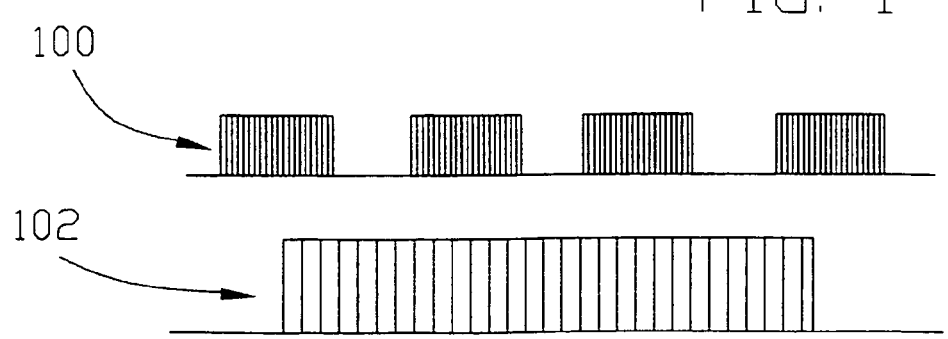
FIG. 4 illustrates a stimulation scheme which may be used for combined stimulation of the dorsal and ventral roots in the present invention.

Qmax = Average maximum flow rate in ml/sec
V (ml) = Average voided volume in ml
Pv (Qmax) = Maximum bladder pressure in cm of water at maximum flow
Pu (Qmax) = Average sphincter pressure in cm of water at maximum flow
Pv max = Maximum bladder pressure in cm of water
Pu max = Maximum sphincter pressure in cm of water FIG. 4 illustrates the stimulus pattern for the combined dorsal and ventral root stimulation of the present invention. An intermittent pulse train 100 is applied to dorsal root 23 via cuff electrode 32, while a continuous pulse train 102 is simultaneously applied to ventral root 22 via cuff electrode 30. In this manner, low pressure bladder activation can be achieved by modulating the reflexes associated with the neural system for micturition control and eliminate the need for dorsal rhizotomies.

Pulse train 100 preferably consists of pulses delivered at a frequency of 10 to 35 Hz, with each pulse having a nominal amplitude of less than 1 ma and a pulse duration of 10 to 100 μsec. Pulse train 100 is generated intermittently, with a pattern of 0.25 to 1 second on/0.25 to 1 second off. Pulse train 102 preferably consists of a continuous series of quasitrapezoidal pulses of 350 to 500 μsec duration and a nominal amplitude of 1 ma delivered at a frequency of 15 to 30 Hz.

While the invention has been shown and described in terms of several preferred embodiments, it will be understood that this invention is not limited to these particular embodiments and that many changes and modifications may be made without departing from the true spirit and scope of the invention as defined in the appended claims.

What is claimed is:

1. A method comprising:
   transmitting a first series of stimulus pulses comprising a quasitrapezoidal pulse train to a sacral ventral root of a patient with a first electrode; and
   simultaneously transmitting a second series of stimulus pulses comprising an intermittent pulse train pattern of 1 second on/1 second off to a sacral dorsal root corresponding to the sacral ventral root of the patient with a second electrode to stimulate the dorsal root;
   wherein both series subdue urethral reflexes and enhances voiding to empty the bladder.

2. The method of claim 1, wherein the first electrode comprises a self-sizing cuff electrode.

3. The method of claim 1, wherein the second electrode comprises a self-sizing cuff electrode.

4. The method of claim 1, wherein the first electrode comprises a surface mounted electrode.

5. The method of claim 1, wherein said second electrode comprises a surface mounted electrode.

6. The method of claim 1, wherein said first series of stimulus pulses comprises a quasitrapezoidal pulse train at 20 Hz.

7. The method of claim 1, wherein said second series of stimulus pulses have a nominal amplitude of 1 ma and a pulse duration of 20 to 100 μsecs.

8. The method of claim 1, wherein said first series of stimulus pulses have a nominal amplitude of 1 ma and a pulse duration of 350 to 500 μsecs.

9. An apparatus for the control of bladder function in a patient by combined stimulation of ventral and dorsal sacral roots, comprising:
   a first electrode adapted to be coupled to a sacral ventral root of a patient further adapted to deliver a first series of stimulus pulses comprising a quasitrapezoidal pulse train;
   a second electrode adapted to be coupled to a sacral dorsal root corresponding to said sacral ventral root and further adapted to deliver a second series of stimulus pulses comprising an intermittent pulse train pattern of 1 second on/1 second off to stimulate the dorsal root;
   and control means, electrically coupled to said first and second electrodes, for generating said first and second pulses simultaneously, wherein both series subdue urethral reflexes and enhance voiding to empty the bladder.

10. The apparatus of claim 9, wherein the first electrode comprises a self-sizing cuff electrode.

11. The apparatus of claim 9, wherein the second electrode comprises a self-sizing cuff electrode.

12. The apparatus of claim 9, wherein the first electrode comprises a surface mounted electrode.

13. The apparatus of claim 9, wherein said second electrode comprises a surface mounted electrode.

14. The apparatus of claim 9, wherein said first series of stimulus pulses comprises a quasitrapezoidal pulse train at 20 Hz.

15. The apparatus of claim 9, wherein said second series of stimulus pulses have a nominal amplitude of 1 ma and a pulse duration of 20 to 100 μsecs.

16. The apparatus of claim 9, wherein said first series of stimulus pulses have a nominal amplitude of 1 ma and a pulse duration of 350 to 500 μsecs.

* * * * *